United States Patent [19]

Zirngibl et al.

[11] 4,210,656
[45] Jul. 1, 1980

[54] IMIDAZOLYL VINYL ETHERS AND PROCESS FOR PREPARING SAME

[75] Inventors: Ludwig Zirngibl, Zofingen; Johanna Fischer, Reiden; Kurt Thiele, Zofingen, all of Switzerland

[73] Assignee: Siegfried Aktiengesellschaft, Zofingen, Switzerland

[21] Appl. No.: 970,312

[22] Filed: Dec. 18, 1978

[30] Foreign Application Priority Data

Dec. 21, 1977 [DE] Fed. Rep. of Germany ....... 2757113

[51] Int. Cl.$^2$ .................. A61K 31/415; C07D 233/60
[52] U.S. Cl. ................. 424/273 R; 542/405; 542/411; 542/413; 542/426; 542/453; 542/458
[58] Field of Search ............... 542/405, 411, 453, 458, 542/426, 413; 424/273 R

[56] References Cited

U.S. PATENT DOCUMENTS

| | | | |
|---|---|---|---|
| 3,462,446 | 8/1969 | DeWald | 542/413 |
| 3,658,797 | 4/1972 | Ross et al. | 542/411 |
| 3,658,813 | 4/1972 | Godefroi et al. | 542/413 |
| 3,839,574 | 10/1974 | Godefroi et al. | 548/341 |
| 4,086,351 | 4/1978 | Batasubramanyan | 542/405 |

OTHER PUBLICATIONS

Buehler et al., Survey of Organic Syntheses, vol. 2, pp. 335–344, N.Y., Wiley, 1977.
Gross et al., Angew. Chem., 1967, vol. 79, pp. 358–362.
Shostakovskii et al., Russian Chem. Rev., 1968, vol. 37, pp. 907–919.

Summers, Chem. Rev., 1955, vol. 55, pp. 301, 314–317 & 336–338.
Hofmann, Imidazoles and Its Derivatives Part I, p. 127, N.Y., Interscience, 1953.
Godefroi et al., J. Med. Chem., 1969, vol. 12, pp. 784–791.

Primary Examiner—Natalie Trousof
Attorney, Agent, or Firm—Burns, Doane, Swecker & Mathis

[57] ABSTRACT

α-Aryl-β-imidazol-1-yl vinyl ethers and their acid addition salts are disclosed, wherein the imidazolyl vinyl ether has the formula:

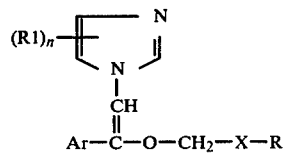

Ar represents a substituted or unsubstituted aryl group, R an alkyl, aryl or aralkyl group, X an oxygen atom, a sulfur atom, a sulfinyl or a sulfonyl group and R1 a lower alkyl group or a nitro group. These compounds are effective wide spectrum fungicides and bactericides. To prepare these vinyl ethers, a corresponding 1-arylacylimidazole is o-alkylated in presence of NaH with a corresponding α-halogen ether, α-halogen thioether, α-halogen sulfinyl compound or a corresponding α-halogen sulfonyl compound.

8 Claims, No Drawings

IMIDAZOLYL VINYL ETHERS AND PROCESS FOR PREPARING SAME

This invention relates to α-aryl-β-imidazol-1-yl vinyl ethers, a process for preparing same and their uses.

1-(β-Aryl) ethyl imidazole derivatives have for some time been known as fungicides and bactericides (German OS 19 40 388 and German OS 20 63 857). Since then numerous attempts have become known seeking to improve the active agents of this class of compounds, especially to increase their effectiveness, to widen the spectrum of their activity and to improve their chemical and physical properties such as their stability and solubility. In the framework of these efforts 1-aryl-2-(imidazol-1-yl) ethene derivatives have also become known from German OS 26 45 617, and especially the 2-keto derivatives. These known compounds are distinguished by a very broad antimycotic activity spectrum, but are unsatisfactory as regards their fungicidal and bactericidal activity, expressed for instance in terms of their minimum blocking concentration.

The invention has as its object the provision of α-aryl-β-imidazol-1-yl vinyl derivatives with quantatively improved activity and the provision of an economical and trouble-free process for preparing these compounds.

In achieving this object, this invention has provided α-aryl-β-imidazol-1-yl vinyl ethers, and their acids addition salts, having the formula

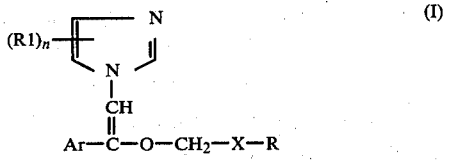

in which
 Ar represents phenyl, naphthyl, or a mono- or dinuclear heterocyclic ring, wherein these rings may be mono- or polysubstituted and the substituents may independently from each other be halogen, lower alkyl, also cycloalkyl, of 1 to 6 carbon atoms, trifluoromethyl, lower alkoxy and lower alkylthio in each case with 1 to 6 carbon atoms in the alkyl portion, phenyl, benzyl, cyano, nitro or amino.
 X represents oxy, thio, sulfinyl or sulfonyl
 R is an unbranched, branched or cyclic, saturated or unsaturated, alkyl of 1 to 12, preferably 1 to 6 carbon atoms, with one or more double or triple carbon bonds, aryl or aralkyl with 1 to 6 carbon atoms in the alkyl portion, wherein "aryl" including any substituents in any given case may have the meaning given above to the residue Ar
 R1 represents a lower alkyl of 1 to 6 carbon atoms or a nitro group and may occur in any desired position in the imidazole ring and
 n is zero, 1, 2 or 3 wherein the individual groups R1 may be different from each other when n is 2 or 3.

These imidazolyl vinyl ethers suprisingly show a distinctly higher activity than the known α-aryl-β-imidazol-1-yl-β-keto vinyl derivatives. In contrast to these known compounds the imidazolyl vinyl ethers have the most important advantage that they produce resistance to a much smaller extent. In contrast to the commercially available α-aryl-β-imidazol-1-yl ethyl ethers that are structurally most closely related, the corresponding imidazolyl vinyl ethers have the advantage of a much wider spectrum and a wider utility with a comparable effectiveness and a somewhat lower tendency to produce resistance.

The bactericidal and fungicidal imidazolyl vinyl ethers of the invention are used as active agents in drugs for use in both human and veterinary medicine as well as in formulations for the protection of vegetation. The imidazolyl vinyl ethers can be used for these purposes singly or in mutual admixture either as free bases or in the form of their acid addition salts, e.g., their hydrochlorides or sulfates, but preferably in the form of their nitrates. They can be combined in the formulations in an otherwise conventional manner with customary companion agents, carriers and diluents. In this, the stereoisomers coming within the scope of formula (I) may be used in pure form as well as in admixture.

The α-aryl-β-imidazol-1-yl vinyl ethers of formula (I) can be produced by reacting the corresponding 1-arylacyl imidazole with a corresponding α-halogen ether:

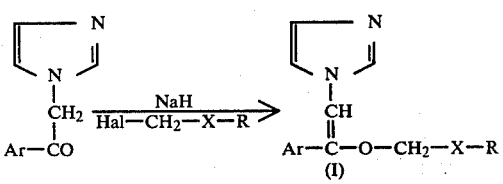

In the foregoing schematically shown chemical equation the residues Ar, R and X have the previously given meaning, whereas Hal represents a halogen atom.

This reaction is preferably carried out in hexamethylphosphoric acid triamide while cooling with ice water in the presence of or after prior reaction with NaH. In the course of the reaction the temperature can rise to 50° or 60° C.

The smooth and practically byproduct free course of this reaction is surprising and was not to be expected from the prior art. Thus for instance Godefroi et al., J. med. chem. 12, page 785, left column, paragraph 3, disclose that the methylation of 1-phenacylimidazole in hexamethylphosophoric acid amide in the presence of NaH leads smoothly to 1-(α-methyl)phenacylimidazole, i.e., that a C-alkylation and no O-alkylation takes place. In a like manner Gross et al., Angew. Chem. 79, pages 359 and 360, disclose the practically exclusive occurrence of C-alkylations when α-halogen ethers and α-halogen thioethers are reacted with enolysable carbonyl compounds. Only in the case of the acetoacetic ester is a certain O-alkylation observed in competition and side by side with C-alkylation (Summers, Chem. Rev. 55, 301). In view of this state of the art is was surprising that the reaction of α-halogen ethers and their sulfur analogs leads smoothly and in an economically practical manner to the corresponding vinyl ethers when reacted with the 1-phenacylimidazole derivatives, that is, that a smooth O-alkylation takes place.

The invention is further illustrated by the following working examples.

EXAMPLE 1

α-(2,4-Dichlorophenyl)-β-imidazol-1-yl-vinyl-methyl-thiomethylether nitrate

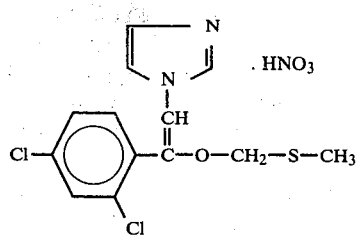

12.75 g (50 mmol) 1-(2,4-dichlorphenacyl)imidazole are disolved in 45 ml hexamethylphosphoric acid triamide in a three-neck flask fitted with attached reflux condenser, an internal thermometer and a dropping funnel. The solution is reacted with 2.5 g (52 mmol) of a 50% dispersion of NaH in refined mineral oil added portionwise in the course of 90 minutes while cooling with ice. Thereafter the mixture is stirred for one hour at a temperature below 10° C. Thereafter the mixture is heated to 50° C. and again stirred for one hour. The reaction mixture is then again cooled to a temperature of from 5° to 10° C. and slowly and dropwise reacted with 5.31 g (55 mmol) chlorodimethylthioether. One then stirs the mixture for two hours at room temperature and then for two more hours while keeping the temperature of the mixture at 50° C. The reaction mixture is then poured into 750 ml water and extracted three times with 200 ml ethyl acetate. The combined extracts are dried with sodium sulfate and the solvent evaporated therefrom at reduced pressure. As residue one obtains 40 g of an oily substance which is purified by chromatography on a silica gel column using dichloromethane as a carrier. The combined clean fractions are evaporated and produce 5.0 g of an oily substance. This residue is dissolved in a mixture of ethyl acetate and diethyl ether and precipitated by means of 3.5 ml of 60% aqueous nitric acid. 4.32 g (11.4 mmol) of the clean nitrate having a melting point 131° to 132.5° C. are obtained. In the IR spectrum taken in KBr the strong ketone band of the starting material at 5.9 μm has disappeared.

| Elemental analysis for $C_{13}H_{12}Cl_2N_2OS \cdot HNO_3$ | | | |
| --- | --- | --- | --- |
| | C (%) | H (%) | N (%) |
| Calculated: | 41.28 | 3.46 | 11.11 |
| Found: | 41.32 | 3.33 | 10.70 |

EXAMPLE 2

α-(2,4-Dichlorophenyl)-β-imidazol-1-yl-vinyl-(2-chlorophenoxy)methylether nitrate

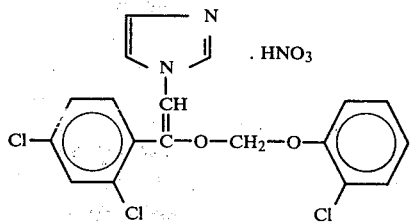

The process described in example 1 is repeated except that instead of the thioether an equivalent amount of 2-chlorophenyl-chloromethyl ether is dropped into the reaction mixture which is again cooled after the addition of the NaH. The reaction mixture is worked up, purified and finally precipitated as a nitrate in the manner described in example 1. The obtained nitrate has a melting point of 141° to 142° C. In a nuclear magnetic proton resonance spectrum in a mixture of deuterated chloroform and dimethylsulfoxide the following displacements are observed: $\delta = 5.47$ (s; 2H; —OCH$_2$O—); $\delta = 6.74$ (1H; C=CH—); $\delta = 9.17$ (s; 1H; imidazol—2—yl—H); $\delta = 6.8$–7.7 (m; 9H; aromat. and heterocycl. protons).

EXAMPLES 3 to 14

The following substances were prepared according to the process described in examples 1 and 2 by reaction of 1-(2,4-dichlorophenacyl)imidazole with the corresponding chloromethyl ethers or their sulfur derivatives in equivalent amounts and, with the exception of example 6, followed by subsequent precipitation as the nitrate:

Ex. 3.

α-(2,4-Dichlorophenyl)-β-imidazol-1-yl-vinylmethoxymethyl-ether nitrate, mp 94° to 96° C.

Ex. 4.

α-(2,4-dichlorophenyl)-β-imidazol-1-yl-vinyl-(4-chlorphenyl-thio)methylether nitrate, mp 140° to 142° C.

Ex. 5.

α-(2,4-Dichlorophenyl)-β-imidazol-1-yl-vinyl-n-butoxymethyl-ether nitrate, mp 95° to 98° C.

Ex. 6

α-(2,4-Dichlorophenyl)-β-imidazol-1-yl-vinylbenzyloxymethyl-ether; the free base is purified by means of a chromatographic column in the manner described in example 1. The purity of the compound is confirmed by means of thin layer chromatography. The elemental analysis for $C_{19}H_{16}Cl_2N_2O_2$ gives the following values:

| | C (%) | H (%) | N (%) | Cl (%) |
| --- | --- | --- | --- | --- |
| Calculated: | 60.81 | 4.30 | 7.47 | 18.90 |
| Found: | 61.01 | 4.64 | 7.21 | 18.52 |

Ex. 7.

α-(2,4-Dichlorophenyl)-β-imidazol-1-yl-vinyl(2,4-dichlorophenoxy)methylether nitrate, mp 141°0 to 142° C.

Ex. 8

α-(2,4-Dichlorophenyl)-β-imidazol-1-yl-vinyl-(4-methoxyphenoxy)methylether nitrate, mp 133° to 133.5° C.

Ex. 9.

α-(2,4-Dichlorophenyl)-β-imidazol-1-yl-vinyl-(5-chloropyrid-2-yl-thio)methylether nitrate, mp 165° to 166° C.

Ex. 10.

α-(2,4-Dichlorophenyl)-β-imidazol-1-yl-vinyl-n-pentyl-thiomethyl-ether nitrate, mp 126° to 127° C.

Ex. 11.

α-(2,4-Dichlorophenyl)-β-imidazol-1-yl-vinylcyclohexyl-thiomethylether nitrate, mp 128° to 129.5° C.

Ex. 12.

α-(2,4-Dichlorophenyl)-β-imidazol-1-yl-vinylethylthiomethylether nitrate, mp 120.5° to 122° C.

Ex. 13.

α-(2,4-Dichlorophenyl)-β-imidazol-1-yl-vinyl-(4-chlorphenoxy)-methylether nitrate, mp 132.5° to 134.5° C.

Ex. 14.

α-(2,4-Dichlorophenyl)-β-imidazol-1-yl-vinylallyl-thiomethylether nitrate, mp 101° to 103° C.

TESTS

The compounds from examples 1 to 14, the commercially available fungicide α-(2,4-dichlorophenyl)-β-imidazol-1-yl-ethyl-(4-chlorophenyl)methylether nitrate (A) and two imidazolylvinyl ketones of a type known from German OS 26 45 617 are comparatively evaluated for their fungicidal and bactericidal activity. The vinyl ketones used as controls in these tests are α-imidazol-1-yl-β-5-bromothien-2-yl-vinyl-2,4-dichlorophenylketone (B) and α-imidazol-1-yl-β-4-nitrophenylvinyl-2,4-dichlorophenyl-ketone (C).

The compounds are tested to determine their minimum blocking concentration (μg/ml) for bacteria and fungi according to the gradient plate method with gradients from zero to 100 μg/ml. In these tests the compounds are used as solutions in 10% dimethylformamide. The results are summarized in Table 1. Staphylococcus aureus haemolyticus (St) and Streptococcus faecalis (Str) are used as bacteria, Candida albicans (Ca), Trichophyton mentagrophytes (Tri) and Aspergillus niger (Asp) are used as fungi.

The cases in which a resistance or a partial resistance was observed are marked "r" in Table 1.

Table 1

| Example No. | Minimum Blocking Concentration (μg/ml) | | | | |
|---|---|---|---|---|---|
| | Bacteria | | Fungi | | |
| | St | Str | Ca | Tri | Asp |
| 1 | 10 | 20 | <10 | <10 | <10 |
| 2 | <10 | 10 | r | <10 | 50r |
| 3 | 70 | 25 | <10 | <10 | <10 |
| 4 | <10 | 50r | r | <10 | <10 |
| 5 | <10 | 10 | r | <10 | <10 |
| 6 | <10 | 30 | r | <10 | <10 |
| 7 | <10 | <10 | r | <10 | <10 |
| 8 | 10 | r | r | <10 | <10 |
| 9 | <10 | <10 | r | <10 | <10 |
| 10 | <10 | <10 | r | <10 | <10 |
| 11 | <10 | <10 | r | <10 | 15 |
| 12 | 10 | 10 | r | <10 | <10 |
| 13 | <10 | 30r | r | <10 | <10 |
| 14 | <10 | <10 | r | <10 | <10 |
| Comparison (Control) | | | | | |
| A | <10 | — | r | <10 | <10 |
| B | r | — | r | <10 | r |
| C | r | 80r | r | 20 | r |

Table 1 shows the compounds of examples 1 and 3 to be particularly desirable fungicides in that among all the compounds tested these two were the only ones that produced no noticeable resistance in the Candida albicans test organisms. However, Table 1 further shows that the compounds of all the examples 1–14 were also in all cases as good as the prior art compounds A and B and better than compound C in controlling the Trichophyton mentagrophytes organism and, with the possible exception of the compound of example 2, all the tested compounds of the invention were as good as or better than the prior art compounds in controlling the Aspergillus niger fungus.

All the tested compounds that are illustrative of the invention also have shown themselves to be superior to prior art compounds B and C in terms of controlling the Staphhylococcus bacteria and at the same time desirably effective in controlling the Streptocci.

The active compounds may be applied to substrates in the form of dusts when diluted with solid carriers such as clays, or in the form of aqueous dispersions or solutions, or they may be included in otherwise contained soaps or synthetic detergent compositions used for washing walls or floors, or hospital laundry, or the like.

The invention is particularly pointed out and claimed in the appended claims.

We claim:

1. An α-aryl-β-imidazol-1-yl vinyl ether having the formula

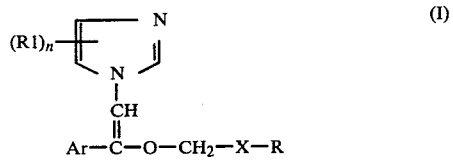

or an acid addition salt thereof acceptable for bactericidal or fungicidal use, in which Ar represents phenyl or naphthyl that is unsubstituted or mono- or poly-substituted with substituents that are independently selected from the group consisting of halogeno, alkyl and cycloalkyl of up to 6 carbon atoms, trifluoromethyl, alkoxy and alkylthio of up to 6 carbon atoms, phenyl, benzyl, cyano, nitro and amino, X represents oxy, thio, sulfinyl or sulfonyl, R is (a) unbranched or branched aliphatic or cycloaliphatic hydrocarbyl of up to 12 carbon atoms which is either saturated or contains one or more double and/or triple carbon bonds or (b) Ar as defined above, R1 represents alkyl of 1 to 6 carbon atoms or nitro and may occur in any desired position in the imidazole ring, and n is zero, 1, 2 or 3 wherein the individual R1 groups are the same or different from each other when n is 2 or 3 provided that only one R1 group may be nitro.

2. An imidazolyl vinyl ether according to claim 1 wherein Ar is 2,4-dichlorophenyl and n is zero.

3. An imidazolyl vinyl ether having the formula

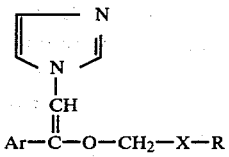

or an acid addition salt thereof which is acceptable for bactericidal or fungidical use, wherein Ar is 2,4-dichlorophenyl, X is oxygen or sulfur and R is an alkyl of 1 to 6 carbon atoms.

4. A compound according to claim 3 wherein R is methyl.

5. α-(2-4-Dichlorophenyl)-β-imidazol-1-yl-vinylmethylthiomethylether nitrate.

6. A process for making a compound as defined in claim 1 which comprises reacting a corresponding 1-arylacylimidazole in the presence of NaH initially at a temperature below 0° C. and thereafter at a temperature up to 50° C. with a corresponding α-halogen ether or α-halogen thioether or α-halogen sulfinyl compound or α-halogen sulfonyl compound, and recovering imidazolyl vinyl ether product from the resulting reaction mixture.

7. A process for controlling bacteria or fungi which comprises applying thereto an effective amount of a compound of claim 1.

8. Process for controlling fungi which comprises applying to the fungi a fungicidal amount of a compound defined in claim 3.